United States Patent [19]

Shawl

[11] 4,172,948
[45] Oct. 30, 1979

[54] PREPARATION OF DIPHENYLMETHANE MONO AND DICARBAMATES AND POLYMETHYLENE POLYPHENYL CARBAMATES

[75] Inventor: Edward T. Shawl, Wallingford, Pa.

[73] Assignee: Atlantic Richfield Company, Los Angeles, Calif.

[21] Appl. No.: 6,047

[22] Filed: Jan. 24, 1979

[51] Int. Cl.$^2$ .................. C07C 125/04; C07C 118/00
[52] U.S. Cl. ........................................ 560/25; 560/27; 260/453 P
[58] Field of Search ..................................... 560/25, 27

[56] References Cited

U.S. PATENT DOCUMENTS

| 2,946,768 | 7/1960 | Klauke | 560/25 |
| 3,873,553 | 3/1975 | Hearsey | 560/25 |
| 3,919,279 | 11/1975 | Rosenthal et al. | 260/453 P |
| 3,962,302 | 6/1976 | Rosenthal et al. | 260/453 P |
| 4,014,914 | 3/1977 | Pistor et al. | 260/453 PH |

FOREIGN PATENT DOCUMENTS 1177557 1/1970 United Kingdom.

Primary Examiner—James O. Thomas, Jr.
Assistant Examiner—G. T. Breitenstein
Attorney, Agent, or Firm—Delbert E. McCaslin

[57] ABSTRACT

Diphenylmethane mono and dicarbamates and polymethylene polyphenyl carbamate homologs and derivatives of these compounds are prepared by employing a superatmospheric pressure of anhydrous hydrogen chloride to catalytically rearrange an (alkoxycarbonyl)-phenylaminomethylphenyl compound having the general formula

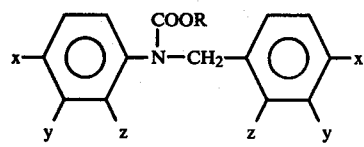

including the higher homologs of such compounds, wherein x, y and z, which are different on the ring, are an alkyl group having from 1 to 3 carbon atoms, an —NHCOOR, —CH$_2$ArNHCOOR or —N(COOR)CH$_2$Ar group; x, y and z may also be at least one hydrogen; R is a 1 to 3 carbon atom alkyl group and Ar is phenyl which may be substituted with a 1 to 3 carbon atom alkyl group.

11 Claims, No Drawings

PREPARATION OF DIPHENYLMETHANE MONO AND DICARBAMATES AND POLYMETHYLENE POLYPHENYL CARBAMATES

FIELD OF THE INVENTION

The present invention relates to a process for the preparation of esters of aromatic carbamic acids (urethanes) particularly diphenylmethane dicarbamates and related higher homologs and derivatives, by the anhydrous hydrogen chloride catalyzed rearrangement of an (alkoxycarbonyl)phenylaminomethylphenyl compound such as 2-[(ethoxycarbonyl)phenylaminomethyl]-phenylcarbamic acid, alkyl ester.

BACKGROUND OF THE INVENTION

Polymeric aromatic carbamic acid esters (polyurethanes) such as diphenylmethane dicarbamates and the related higher homologs polymethylene polyphenyl carbamates have become increasingly important products particularly, for use in the preparation of the commercially valuable diphenylmethane diisocyanates and mixtures of diisocyanates and the polyisocyanates by the decomposition of such polymeric aromatic carbamic acid esters in a suitable solvent as shown in Rosenthal et al, U.S. Pat. Nos. 3,962,302, June 8, 1976 and 3,919,279, Nov. 11, 1975.

At the present time there is no known successful commercial method for the direct preparation of polymeric aromatic esters of carbamic acid. The corresponding diphenylmethane diisocyanates and polyisocyanates, available commercially, are largely produced by the phosgenation of mixtures of diamines and polyamines obtained by the condensation of aniline and formaldehyde with catalytic quantities of a mineral acid as for example, disclosed in the Pistor et al, U.S. Pat. No. 4,014,914.

A proposed prior art process for the preparation of polymeric aromatic carbamic acid esters (polyurethanes) is disclosed in Klauke et al, U.S. Pat. No. 2,946,768 and involves the condensation of aryl carbamic acid esters with carbonyl compounds in a dilute aqueous acid condensation medium. However, in such process the carbonyl compound such as formaldehyde tends to react at the nitrogen of the carbamate to produce, along with desired polyurethanes, varying amounts, i.e., generally between 15 percent and 50 percent by weight, of undesirable (alkoxycarbonyl)-phenylaminomethylphenyl compounds which includes the various dimers, trimers, tetramers, etc. of such compounds (also referred to herein as "N-benzyl" compounds). Attempts to prepare mono or diisocyanates and polyisocyanates or to otherwise use the mixture containing the undesired N-benzyl compounds, which cannot be converted to an isocyanate by pyrolysis, and polyurethanes presents many problems since there is no known method for separating the polyurethanes from the N-benzyl impurities.

SUMMARY OF THE INVENTION

This invention relates to a process for the preparation of diphenylmethane mono and dicarbamates and the higher molecular weight homologs, polymethylene polyphenyl carbamates, which comprises catalytically rearranging an (alkoxycarbonyl)phenylaminomethylphenyl compound (N-benzyl compound) with a superatmospheric pressure of anhydrous hydrogen chloride. More specifically, the present invention concerns a method for the preparation of the carbamates by employing anhydrous hydrogen chloride under pressure to catalyze the rearrangement of the N-benzyl compounds produced, in addition to urethanes, as side products by the condensation of lower alkyl esters of phenyl carbamic acid with carbonyl compounds, such as formaldehyde, in the presence of an aqueous acid solution as described for example in the aforementioned U.S. Pat. No. 2,946,768 and incorporated herein by reference. The product mixture produced by such condensation process containing diurethanes and polyurethanes, N-benzyl compounds, unreacted alkylphenylcarbamates and other by-products such as amines may be contacted at temperatures of from about 35° C. to 170° C. with an anhydrous hydrogen chloride at a pressure of from about 50 psig to 600 psig to catalytically convert or rearrange said N-benzyl compounds to the desired mono-, di- and polyurethanes. Alternatively, the unreacted alkylphenylcarbamate may be removed from the mixture by, for example, vacuum distillation prior to treatment. The anhydrous hydrogen chloride rearrangement of the N-benzyl compounds resulting from other methods of preparation, as hereinafter described, is also contemplated by the method of the present invention.

Aqueous hydrochloric acid as well as anhydrous hydrogen chloride employed at atmospheric pressure are unsatisfactory as catalysts for the rearrangement of the (alkoxycarbonyl)phenylaminomethylphenyl compounds as hereinafter described.

It is an object of this invention therefore to provide a process for the preparation of diphenylmethane mono and dicarbamates and the related polymethylene polyphenyl carbamates in high yield by the conversion or rearrangement of (alkoxycarbonyl)phenylaminomethylphenyl compounds employing a superatmospheric pressure of anhydrous hydrogen chloride as a catalyst.

It is another object of this invention to provide a process for the anhydrous hydrogen chloride catalyzed conversion or rearrangement of (alkoxycarbonyl)-phenylaminomethylphenyl compounds formed during the preparation of di- and higher polymeric carbamic acid esters by the dilute aqueous acid condensation of N-aryl carbamic acid esters such as ethylphenylcarbamate with a carbonyl compound to the useful di and polyurethane compounds.

These and other objects and advantages of this invention will become apparent from the description of the invention which follows and from the claims.

DESCRIPTION OF THE INVENTION

In accordance with the present invention, an (alkoxycarbonyl)phenylaminomethylphenyl compound having the general formula

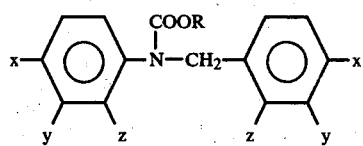

including the higher homologs of such compounds, wherein x, y and z, which are different on the ring, are an alkyl group having from 1 to 3 carbon atoms, an —NHCOOR, —CH$_2$ArNHCOOR or —N(COOR)CH$_2$Ar group; x, y and z may also be at least one hydrogen;

R is a 1 to 3 carbon alkyl group and Ar is phenyl which may be substituted with a 1 to 3 carbon atom alkyl group, is contacted at temperatures of from about 35° C. to 170° C., with a catalytic amount of an anhydrous hydrogen chloride at a superatmospheric pressure of from about 50 psig to 600 psig, with or without the addition of an inert solvent, to catalytically convert or rearrange the (alkoxycarbonyl)phenylaminomethylphenyl compound mixture to mono or dicarbamates and polymethylene polyphenyl carbamates and derivatives. The preparation of a diphenylmethane dicarbamate, diethyl ester, for example, is carried out according to the following postulated equation employing 2-[(ethoxycarbonyl)phenylaminomethyl]phenylcarbamic acid, ethyl ester:

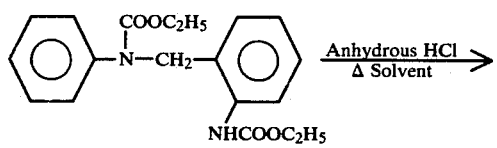

2-[(ethoxycarbonyl)phenylaminomethyl]phenylcarbamic acid, ether ester

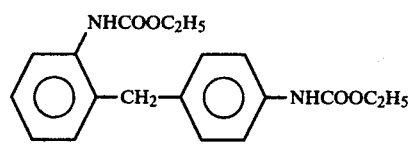

2,4'-methylenebis(phenylcarbamic acid), diethyl ester; (diphenylmethane-2,4'-dicarbamate, diethyl ester)

The anhydrous hydrogen chloride catalyzed rearrangement reaction may be carried out in any suitable pressure reactor which is generally equipped with a means for agitation. A general procedure is to charge the N-benzyl compounds together with a solvent, if desired, into the reaction vessel, pressurize with anhydrous HCl and then heat the mixture to the desired temperature for the appropriate period maintaining the desired HCl pressure. The reaction may be carried out batchwise or as a continuous process and the order of addition of the materials may be varied to suit the particular apparatus employed. Upon completion of the reaction the gas is vented and the reaction products recovered and treated by any conventional method such as extraction of the acid medium with water or neutralization with a base and the separation of the resulting phases as well as distillation to remove acid and any solvent employed.

The (alkoxycarbonyl)phenylaminomethylphenyl compounds which may be converted or rearranged by the process of the present invention and characterized by the general formula above include, for example, those compounds which may conform to the following formulae wherein R is an alkyl group containing from 1 to 3 carbon atoms:

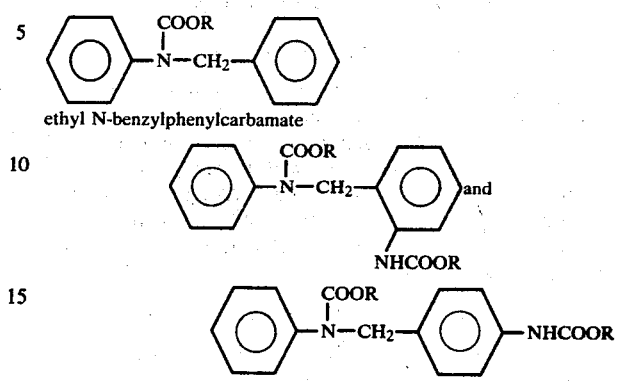

2- and 4-[(alkoxycarbonyl)phenylaminomethyl]phenylcarbamic acid, alkyl ester respectively,

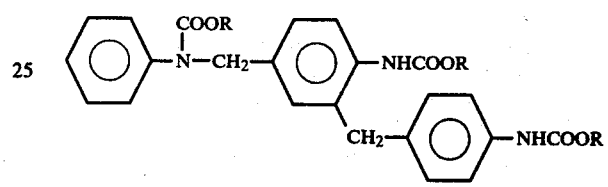

4-[(alkoxycarbonyl)phenylaminomethyl]-2,4'-methylenebis(phenylcarbamic acid), dialkyl ester,

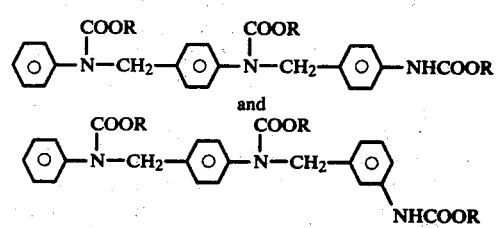

4 and 3[4-[(alkoxycarbonyl)phenylaminomethyl]phenyl(alkoxycarbonyl)aminomethyl]phenylcarbamic acid, alkyl ester respectively; and

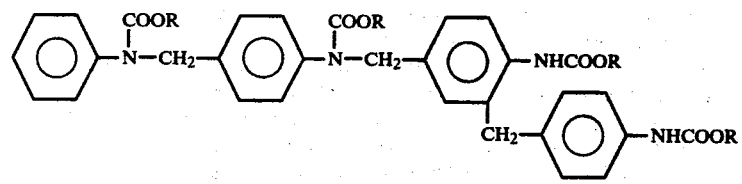

4-[4-[(alkoxycarbonyl)phenylaminomethyl]phenyl(alkoxycarbonyl)aminomethyl]-2,4'-methylenebis(phenylcarbamic acid), dialkyl ester.

These (alkoxycarbonyl)phenylaminomethylphenyl compounds specifically shown by formula and named are obviously merely representative of other N-benzyl compounds, especially the various isomers of such compounds which fall within the definition of the general formula hereinabove described for the compounds which can be converted or rearranged to the desired carbamates especially the polycarbamates by the method of this invention. In general, the ethyl esters, i.e., where R is a $C_2H_5$ group and which are produced during the condensation of ethylphenylcarbamate (phenylurethane) with a carbonyl compound such as formaldehyde, are preferred for the preparation of the diethyl esters of diphenylmethane dicarbamate and polymethylene polyphenyl carbamates which may be decomposed to the valuable polymeric isocyanates as hereinabove described.

As indicated above, the reaction product including the N-benzyl compounds which result in unseparable side products during the condensation of alkyl esters of phenyl carbamic acid such as ethylphenylcarbamate with carbonyl compounds such as formaldehyde in the presence of the dilute aqueous acid solution may be processed according to the method of the present invention as such or after removal of the ethylphenylcarbamate unreacted starting material. In addition, N-benzyl compounds which may be produced by other known methods can be employed in the present process. For example, N-phenylbenzylamine and alkylchloroformate, e.g., methyl, ethyl or propylchloroformate may be reacted to prepare the appropriate alkyl N-benzylphenylcarbamate. N-phenyl-2-aminobenzylamine and N-phenyl-4-aminobenzylamine prepared according to the process shown in British Pat. No. 1,177,557, 1 January, 1970, may be reacted with an excess of the alkylchloroformate, such as ethylchloroformate, to produce 2- and 4-[(ethoxycarbonyl)phenylaminomethyl]phenylcarbamic acid, ethyl ester respectively. The 2- and 4-[(alkoxycarbonyl)phenylaminomethyl]phenylcarbamic acid, alkyl esters may also be prepared by reacting a substituted benzyl alcohol such as for example a carbamic acid, benzyl hydroxy, ether ester (ethylphenylcarbamate-2-methylol) with ethylphenylcarbamate and an acid catalyst.

The anhydrous hydrogen chloride employed as catalyst in the present invention is a toxic fuming gas which is very soluble in water and is generally prepared by fractional distillation of hydrochloric acid under pressure or independent of the acid processes, by passing a source of hydrogen over anhydrous calcium chloride. In the process of the present invention the reaction is carried out for the specified period under the desired pressure of hydrogen chloride for rearrangement of the N-benzyl compounds to the desired carbamates.

Although the process of the present invention may be carried out in the absence of solvent, particularly, at the higher temperature of reaction, i.e., 100° C. and above, solvents or mixtures of solvents which are stable and chemically inert to the components of the reaction system may be and are preferably employed due to the viscosity of the mixture of N-benzyl compounds in the form of dimers, trimers, tetramers, etc. Suitable solvents which are employed essentially in an anhydrous condition and generally in amounts of from 0 to 80 weight percent based on the reaction mixture include, for example, nitrated and halogenated aromatic hydrocarbons having up to 12 carbon atoms such as nitrobenzenes, nitrotoluenes, dichlorobenzene, dibromobenzene, alkanes and substituted alkanes, having up to 16 carbon atoms, such as n-pentanes, isopentane, n-hexane, 2-methylpentane, n-heptane, 3,4-dimethylhexane, 2-methylhexane, 3-ethylpentane, cyclopentane, cyclohexane, methylcyclohexane, ethylcyclopentane, cyclooctane, chloroform, carbon tetrachloride, dichloroethane, etc. Nitrobenzene, nitrotoluene and dichlorobenzene are the preferred solvents. Greater amounts of solvent, may be employed but generally are not necessary due to the added burden of recovery. While as indicated above, mixtures of solvents may be employed, it is preferable to use individual solvents in order to alleviate any recovery problem.

As indicated above, the reaction of the present invention can be suitably performed by charging the N-benzyl compounds contained in a condensate or otherwise, together with solvent into a suitable pressure reactor while maintaining reaction conditions essentially anhydrous, pressurizing with anhydrous hydrogen chloride to the desired reaction pressure and then heating the mixture to the desired temperature. The reaction will proceed at temperatures of from about 35° C. to 170° C. It is generally preferred to operate the process at temperatures of from 50° C. to 130° C. to obtain a convenient rate of reaction. Heating and/or cooling means may be employed interior and/or exterior of the reaction to maintain the temperature within the desired range.

The process of the present invention is carried out at hydrogen chloride pressures of from about 50 psig to 600 psig and preferably at pressures of from 75 psig to 250 psig. Higher pressures may be employed but provide no apparent advantage.

The reaction time is generally dependent upon the mixture of N-benzyl compounds being reacted, or condensate being processed, temperature and pressure being employed and will vary dependent on whether the process is continuous or batch but will generally range between about a few minutes and several hours.

The followinng examples are provided to illustrate the invention in accordance with the principles of this invention but are not to be construed as limiting the invention in any way except as indicated by the appended claims.

Although the process of this invention will be directed primarily to the preparation of diphenylmethane dicarbamate, ethyl esters and the polymethylene polyphenyl carbamates, ethyl esters by the pressurized anhydrous hydrogen chloride catalyzed conversion or rearrangement of (ethoxycarbonyl)phenylaminomethylphenyl carbamic acid, ethyl ester, including the higher homolog trimers, tetramers, etc., which are produced for example as side products by the condensation of ethylphenylcarbamate and a carbonyl compound as hereinabove described, it is not intended that the process be limited to such (ethoxycarbonyl)phenylaminomethylphenyl carbamic acid compounds and those skilled in the art will recognize that the present invention is broadly applicable to the treatment of other (alkoxycarbonyl)phenylaminomethylphenyl compounds such as the methyl and propyl esters and higher homologs.

In the Examples (except Comparative Example 1) which follow, the reactions were run in a 6 oz. pressure reactor (Fisher-Porter Tube) fitted with a magnetic stirrer, and thermocouple. The reactants were charged to the reactor and the reactor immersed into a constant temperature oil bath. At the end of the reaction time, gas pressure was released, water was added to the flask to extract the dissolved hydrogen chloride catalyst and the water phase was removed. Conversion of the N-benzyl compounds charged and product yield and distribution was determined by high speed liquid chromatography.

EXAMPLE 1

(Comparative)

A condensation product from the reaction product of ethylphenylcarbamate with a 30 percent formaldehyde solution and 37 weight percent hydrochloric acid in water was prepared according to Example 2 of U.S. Pat. No. 2,946,768 and contained approximately 33 percent unreacted ethylphenylcarbamate, 38 percent diphenylmethane dicarbamates (2,4'- and 4,4'-isomers), 4 percent triurethanes, 15 percent N-benzyl compound dimer (2 and 4-[(ethoxycarbonyl)phenylaminomethyl]-phenylcarbamic acid, ethyl ester, 8 percent N-benzyl compound trimers such as 4[(ethoxycarbonyl)-phenylaminomethyl]2,4'-methylenebis(phenylcarbamic acid) diethyl ester and a small amount of other unidentified by-products. 6.0 g. of the condensation reaction product along with 6.0 g. nitrobenzene solvent and 6.0 g. of 37 weight percent hydrochloric was charged to a 100 ml. three neck reaction flask fitted with a mechanical stirrer, reflux condenser and thermometer and the flask immersed in a constant temperature oil bath. The reaction was carried out at 120° C. for a period of 4 hours. After completion of the reaction water was added to extract the acid. Analysis of the product showed that only 2 percent of the contained N-benzyl compounds were rearranged to di or triurethane products.

EXAMPLE 2

A number of runs were carried out according to the process of the present invention, with a condensation reaction product obtained from the reaction at 80° C. for 1 hour of ethylphenylcarbamate (120 g.) with a 51 percent aqueous formaldehyde solution (20.8 g.) 120 g. nitrobenzene and 125 g. of 60 weight percent sulfuric acid. The condensation reaction product contained approximately 20 percent unreacted ethylphenylcarbamate, 39.9 percent diphenylmethane dicarbamates (2,4'- and 4,4'-isomers), 17.9 percent tri and higher polymeric urethanes and 22.2 percent N-benzyl compound dimers, trimers and higher homologs. 12 g. of the condensation reaction product in a nitrobenzene solvent was charged to the pressure (Fisher-Porter) reactor tube which was pressurized with anhydrous hydrogen chloride and heated to the appropriate temperature for the desired period while maintaining the HCl pressure. Reaction conditions, weight percent condensate in nitrobenzene and the analytical results are set forth in Table 1. Run No. 1 is a comparative run wherein atmospheric pressure was employed.

TABLE 1

| Run No. | Wt. %[1] Condensate | Temp. °C. | Anhydrous HCl Pressure psig. | Time mins. | % N-benzyl[3] Compound Conversion |
|---|---|---|---|---|---|
| 1[2] | 13.8 | 80 | 0 (atmospheric) | 60 | 11 |
| 2 | 13.8 | 80 | 125 | 120 | 100 |
| 3 | 13.8 | 100 | 250 | 75 | 99.8 |
| 4 | 13.8 | 120 | 85 | 120 | 100 |
| 5 | 5.0 | 80 | 125 | 30 | 98.3 |
| 6[4] | 13.8 | 60 | 500 | 30 | 96.0 |

[1]Weight per cent condensation reaction product in nitrobenzene.
[2]Comparative run - atmospheric pressure.
[3]Total per cent conversion of dimers, trimers, tetramers, etc. contained in condensate.
[4]Reaction carried out in a 300 cc. Hasteloy Autoclave with 30 g. of condensation reaction product.

EXAMPLE 3

A number of runs were carried out according to the process of the present invention with a condensation reaction product obtained from the 80° C. reaction of 120 g. of ethylphenylcarbamate with a 51 percent aqueous formaldehyde solution (24.9 g.), 120 g. nitrobenzene and 100 g. of 65 weight percent sulfuric acid. The condensation reaction product contained approximately 12 percent unreacted ethylphenylcarbamate, 28.2 percent diphenylmethane dicarbamates (2,4'- and 4,4'-isomers), 31.0 percent tri and higher polymeric urethanes and 28.8 percent N-benzyl compound dimers, trimers and higher homologs. 12 g. of the condensation reaction product in a nitrobenzene solvent was charged to the pressure (Fisher-Porter Tube) reactor which was pressurized with anhydrous hydrogen chloride and heated to the appropriate temperature for the appropriate period while maintaining the HCl pressure. Reaction conditions, weight percent condensate in nitrobenzene and the analytical results are set forth in Table 2.

TABLE 2

| Run No. | Wt. % Condensate | Temp. °C. | Anhydrous HCl Pressure psig. | Time Min. | % N-benzyl[2] Compound Conversion |
|---|---|---|---|---|---|
| 1 | 82.7 | 80 | 200 | 120 | 88.5 |
| 2 | 41.4 | 80 | 125 | 60 | 100 |
| 3 | 41.4 | 80 | 50 | 120 | 96.4 |
| 4 | 27.5 | 50 | 250 | 120 | 89.8 |

[1]Weight per cent condensation reaction product in nitrobenzene.
[2]Total per cent conversion of dimers, trimers, tetramers, etc. contained in condensate.

EXAMPLE 4

A number of runs were carried out in a solvent employing 12 g. of a condensation reaction product of ethylphenylcarbamate with a 37 percent aqueous formaldehyde solution, 85 percent commercial grade phosphoric acid and water prepared by the process of U.S. Pat. No. 2,946,768. The condensate contained approximately 29 percent unreacted ethylphenylcarbamate, 43 percent diphenylmethane dicarbamate (2,4'- and 4,4'-isomers) 5 percent tri and higher polymeric urethanes and 23 percent N-benzyl compound dimers, trimers and higher homologs. The reaction product was analyzed by high speed liquid chromatography for N-benzyl compound rearrangement. The results are set forth in Table 3 below.

TABLE 3

| Run No. | Wt. % Condensate | Temp. °C. | Anhydrous HCl Pressure psig. | Time mins. | Solvent | % N-benzyl[1] Compound Conversion |
|---|---|---|---|---|---|---|
| 1 | 40 | 80 | 125 | 60 | nitrotoluene | 100 |
| 2 | 40 | 100 | 100 | 90 | dichlorobenzene | 95.5 |

TABLE 3-continued

| Run No. | Wt. % Condensate | Temp. °C. | Anhydrous HCl Pressure psig. | Time mins. | Solvent | % N-benzyl[1] Compound Conversion |
| --- | --- | --- | --- | --- | --- | --- |
| 3 | 40 | 70 | 200 | 60 | dichloroethane | 93.0 |

[1]Total per cent conversion of dimers, trimers, tetramers, etc. contained in condensate.

I claim:

1. A process for the preparation of a diphenylmethane mono and dicarbamate and polymethylene polyphenyl carbamate homologs and derivatives which comprises reacting under substantially anhydrous conditions, (alkoxycarbonyl)phenylaminomethylphenyl compound having the formula

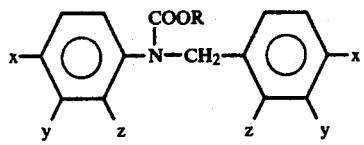

and the higher homologs of said compounds, wherein x, y and z, which are different on the ring are an alkyl group of from 1 to 3 carbon atoms, an —NHCOOR, —CH₂ArNHCOOR or —N(COOR)CH₂Ar group, R is a 1 to 3 carbon alkyl group and Ar is phenyl which may be substituted with an alkyl group of from 1 to 3 carbon atoms; x, y and z may also be at least one hydrogen; at a temperature in the range of from about 35° C. to 170° C. in the presence of an effective amount of an anhydrous hydrogen chloride catalyst at a pressure of from about 50 psig to 600 psig to rearrange the (alkoxycarbonyl)phenylaminomethylphenyl compounds to the mono and dicarbamates and polymethylene polyphenylcarbamates and derivatives and recovering the desired carbamate.

2. A process according to claim 1 wherein the (alkoxycarbonyl)phenylaminomethylphenyl compound is derived from the condensation reaction of an N-aryl carbamic acid ester with a carbonyl compound in the presence of an acid solution.

3. A process according to claim 2 wherein the N-arylcarbamic acid ester is ethylphenylcarbamate.

4. A process according to claim 2 wherein the carbonyl compound is formaldehyde.

5. A process according to claim 1 wherein the (alkoxycarbonyl)phenylaminomethylphenyl compound is the ethyl ester of 2-[(ethoxycarbonyl)phenylaminomethyl]-phenylcarbamic acid or 4-[(ethoxycarbonyl)phenylaminomethyl]phenylcarbamic acid.

6. A process according to claim 1 wherein the reaction is carried out at a temperature in the range of from about 50° C. to 130° C.

7. A process according to claim 1 wherein the anhydrous hydrogen chloride is employed at a pressure of from about 75 psig to 250 psig.

8. A process according to claim 1 wherein the reaction is carried out in the presence of a solvent selected from the group consisting of nitrated and halogenated hydrocarbons having up to 12 carbon atoms, and alkanes and substituted alkanes having up to 16 carbon atoms.

9. A process according to claim 8 wherein the solvent is nitrobenzene, nitrotoluene or dichlorobenzene.

10. A process according to claim 9 wherein the solvent is nitrobenzene.

11. A process for the preparation of a diphenylmethane dicarbamate, diethyl ester, which comprises reacting the ethyl ester of 2-[(ethoxycarbonyl)phenylaminomethyl]phenylcarbamic acid or 4-[(ethoxycarbonyl)phenylaminomethyl]phenylcarbamic acid derived from the condensation reaction of ethylphenylcarbamate with a carbonyl compound in the presence of an aqueous acid solution, at a temperature in the range of from about 50° C. to 130° C. in the presence of an anhydrous hydrogen chloride catalyst at a pressure of from about 75 psig to 250 psig and recovering the desired diphenylmethane dicarbamate.